(12) United States Patent
May

(10) Patent No.: US 7,300,439 B2
(45) Date of Patent: Nov. 27, 2007

(54) POROUS RESORBABLE GRAFT FIXATION PIN

(75) Inventor: Thomas C. May, Wrentham, MA (US)

(73) Assignee: DePuy Mitek, Inc., Raynham, MA (US)

(*) Notice: Subject to any disclaimer, the term of this patent is extended or adjusted under 35 U.S.C. 154(b) by 659 days.

(21) Appl. No.: 10/602,797

(22) Filed: Jun. 24, 2003

(65) Prior Publication Data

US 2004/0267263 A1    Dec. 30, 2004

(51) Int. Cl.
*A61B 17/56* (2006.01)
(52) U.S. Cl. .......................................... 606/72; 606/73
(58) Field of Classification Search ............ 606/60–61, 606/72–73; 433/172–174
See application file for complete search history.

(56) References Cited

U.S. PATENT DOCUMENTS

| | | | |
|---|---|---|---|
| 4,257,411 A | | 3/1981 | Cho |
| 4,711,234 A | * | 12/1987 | Vives et al. ................... 606/60 |
| 5,129,904 A | | 7/1992 | Illi |
| 5,236,431 A | * | 8/1993 | Gogolewski et al. ......... 606/72 |
| 5,249,899 A | | 10/1993 | Wilson |
| 5,350,380 A | | 9/1994 | Goble et al. |
| 5,354,300 A | | 10/1994 | Goble et al. |
| 5,393,302 A | | 2/1995 | Clark et al. |
| 5,397,356 A | | 3/1995 | Goble et al. |
| 5,431,651 A | | 7/1995 | Goble |
| 5,470,334 A | * | 11/1995 | Ross et al. .................... 606/72 |
| 5,562,671 A | | 10/1996 | Goble et al. |
| 5,601,562 A | | 2/1997 | Wolf et al. |
| 5,674,224 A | | 10/1997 | Howell et al. |
| 5,688,284 A | | 11/1997 | Chervitz et al. |
| 5,849,013 A | | 12/1998 | Whittaker et al. |
| 5,868,749 A | | 2/1999 | Reed |
| 5,891,150 A | | 4/1999 | Chan |
| 6,048,343 A | | 4/2000 | Mathis et al. |
| 6,280,472 B1 | | 8/2001 | Boucher et al. |
| 6,939,135 B2 | * | 9/2005 | Sapian ....................... 433/174 |
| 2001/0007074 A1 | | 7/2001 | Strobel et al. |
| 2001/0021852 A1 | | 9/2001 | Chappius |
| 2002/0087160 A1 | | 7/2002 | Clark et al. |
| 2002/0133165 A1 | | 9/2002 | Whittaker et al. |
| 2003/0065361 A1 | * | 4/2003 | Dreyfuss .................... 606/232 |
| 2004/0225292 A1 | * | 11/2004 | Sasso et al. .................. 606/73 |

FOREIGN PATENT DOCUMENTS

| DE | 199 49 285 | 5/2001 |
|---|---|---|
| EP | 0 491 983 | 7/1992 |

OTHER PUBLICATIONS

Kunihiro et al., "In-Vivo Decomposition Absorptive Screw," *Patent Abstracts of Japan*, JP: 2000-166937, vol. 2000, No. 9.
Dialog English Abstract, JP 2000166937 A, "Decomposition Absorptive Screw".
Dialog English Abstract, DE 199 49 285/WO 200126568 A1, Bone Screw.

* cited by examiner

*Primary Examiner*—Michael A. Brown
(74) *Attorney, Agent, or Firm*—Nutter, McClennen & Fish LLP

(57) ABSTRACT

A bioimplantable tissue fixation device is provided for use in repairing and replacing torn or damaged connective tissue such as ligaments and tendons. The device includes an elongate body formed of a bioresorbable material including an outer surface, a proximal end, a distal end and a longitudinal axis extending therethrough. The body includes an internal cavity open at the proximal end which terminates proximal to the distal end. The internal cavity is in fluid communication with at least one opening formed in the outer surface of the body. The internal cavity is able to accept a treatment material for delivery external to the outer surface of the body through the at least one opening at the proximal end.

30 Claims, 7 Drawing Sheets

POROUS RESORBABLE GRAFT FIXATION PIN

FIELD OF THE INVENTION

This invention relates to tissue fixation devices, and to methods for repairing and replacing torn or damaged connective tissue such as ligaments and tendons.

BACKGROUND OF THE INVENTION

The complete or partial detachment of ligaments, tendons or other soft tissues from their associated bones within the body is a relatively common injury, particularly among athletes. Such injuries generally result from excessive stresses being placed on these soft tissues. For example, a tissue-detaching injury may occur as the result of an accident such as a fall, overexertion during a work-related activity, during the course of an athletic event, or in any one of many other situations and/or activities.

In the case of a partial detachment, commonly referred to under the general term "sprain," the injury will frequently heal itself, if given sufficient time, and if care is taken not to expose the injury to any undue or extraordinary stress during the healing process. If, however, the ligament or tendon is completely detached from its associated bone or bones, or if it is severed as the result of a traumatic injury, partial or permanent disability may result. Fortunately, a number of surgical techniques exist for re-attaching such detached tissues and/or completely replacing severely damaged tissues.

One such technique involves the re-attachment of the detached tissue using traditional attachment devices such as metal staples, sutures, and cancellous bone screws. Such "traditional" attachment devices have also been used to attach tendon or ligament substitutes (often formed of autogeneic tissue harvested from elsewhere in the body) to the desired bone or bones. Another technique is described in detail in U.S. Pat. No. 4,950,270 entitled "Cannulated Self-Tapping Bone Screw" to Bowman et al. In this technique, an anterior cruciate ligament in a human knee, for example, is replaced and/or repaired by forming bone tunnels through the tibia and/or femur at the points of normal attachment of the anterior cruciate ligament. A ligament graft, with a bone plug on at least one of its ends, is sized to fit within the bone tunnels. Suture is then attached to the outer end of each bone plug, and thereafter passed through the femoral and/or tibial bone tunnels. The femoral plug and/or the tibial plug is/are then inserted into the appropriate bone tunnel behind the suture. Subsequently, the suture is drawn tight (simultaneously in opposite directions, in cases where bone plugs are to be located in both a femoral bone tunnel and a tibial bone tunnel). This procedure positions the bone plug (or plugs) in the desired location, and imparts the desired degree of tension to the ligament or ligament substitute. Finally, while holding the bone plugs in position, a bone screw is inserted between each bone plug and the side wall of its associated bone tunnel so as to securely lock the bone plug in position using a tight interference fit.

Another attachment technique is described in U.S. Pat. No. 5,849,013 entitled "Method and Apparatus for Fixing a Bone Block in a Bone Tunnel" to Whittaker et al., which is incorporated herein by reference in its entirety. This patent describes a cross pin system for ACL reconstruction. In such a system, a drill guide is used to direct a pin, screw or rod transversely into a bone tunnel in the tibia or femur so as to lock a replacement ligament in the bone tunnel.

With the advancement of anterior cruciate ligament surgery from the open reconstructions to arthroscopic-endoscopic reconstructions, surgeons are faced with a number of choices concerning graft fixation, both at the femur and the tibia. These ligament fixation devices have been introduced to the orthopaedic community, often with mechanical studies that bear little relevance to the actual demands of postsurgical rehabilitation and return to sports mechanics. Thus, it can be difficult for the surgeon to determine those fixation devices that will prove the most reliable during early healing stages.

A number of principles have been established in the last decade concerning anterior cruciate ligament (ACL) surgery, which when adhered to usually result in an excellent outcome. Anatomic placement, no femoral condylar notch impingement, early range of motion, and strong, rigid fixation are but a few of these important principles. Some current devices, however, cannot withstand repeated cycling motions without loss of fixation strength. Moreover, depending on the fixation point of the graft within the bone tunnel, the graft can wear against the bone eventually resulting in tearing or breakage of the graft.

Successful reconstruction depends on a number of additional factors, including the desire to allow patients to return to their normal daily activities as soon as possible. In order for this goal to be achieved, it is important to facilitate rapid healing and to maintain the stability and fixation of the graft.

Despite existing technology and techniques, there remains a need for tissue fixation devices that promote rapid healing while maintaining a strong rigid fixation, and that avoid the risk of tearing or breakage of the graft.

SUMMARY OF THE INVENTION

The present invention generally provides a bioimplantable tissue fixation device including an elongate body formed of a biocompatible, bioresorbable material and having an outer surface, a proximal end, a distal end and a longitudinal axis extending therethrough. An internal cavity located within the body opens at the proximal end of the fixation device and terminates proximal to the distal end of the device. The outer surface of the body includes at least one opening that is in fluid communication with the internal cavity such that the internal cavity is able to accept a treatment material for delivery external to the outer surface of the body through the at least one opening. In one embodiment, the tissue fixation device may be a pin adapted to secure bone and/or a soft tissue graft.

In another aspect of the invention, the device may have surface features on at least a portion of the outer surface of the elongate body for holding the elongate body in position after it has been implanted. Such surface features may include, but are not limited to, roughened regions, threads, barbs, hooks, and combinations thereof. In another embodiment of the invention, the fixation device has a smooth outer surface.

In one embodiment of the present invention, the outer surface of the elongate body may be porous and the at least one opening in the outer surface may be formed from a pore matrix extending between the internal cavity and the outer surface. In yet another embodiment, the at least one opening in the outer surface of the body communicates with the internal cavity through a passageway. Preferably, the passageway extends through a non-porous outer body surface.

The treatment material delivered with the device of the present invention may be a biologically active material such as tissue fragments, growth factors, matrix proteins, peptides, antibodies, enzymes, cytokines, viruses, nucleic acids, peptides, isolated cells, platelets and combinations thereof. The treatment material may also be an adhesive agent.

The invention also contemplates a method of using the tissue fixation device.

DETAILED DESCRIPTION OF THE INVENTION

The present invention provides a bioimplantable, resorbable device that is able to affix bone (including bone segments) and/or soft tissue grafts, such as ligament and tendon grafts, within a patient. The device is adapted to be implanted in a bone tunnel to securely affix the tissue graft to the bone. One advantageous feature of the device is that it includes one or more channels formed therein to enable the delivery of a treatment material, such as a biological agent, to facilitate improved fixation and/or more rapid healing.

Figure 1:
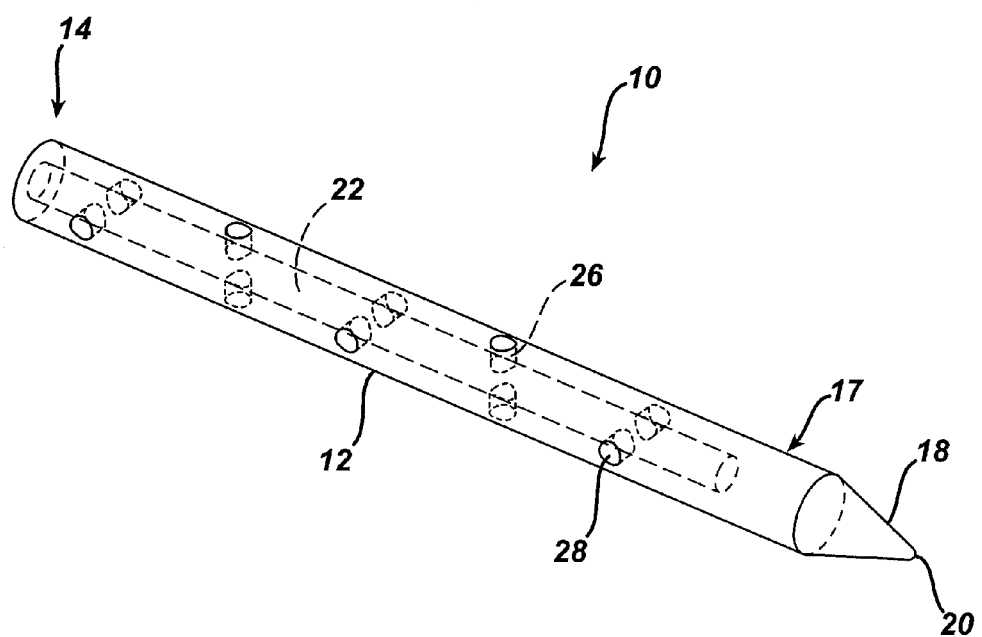
FIG. 1 is a partially transparent view of one embodiment of the tissue fixation device shown in perspective.
Figure 2:
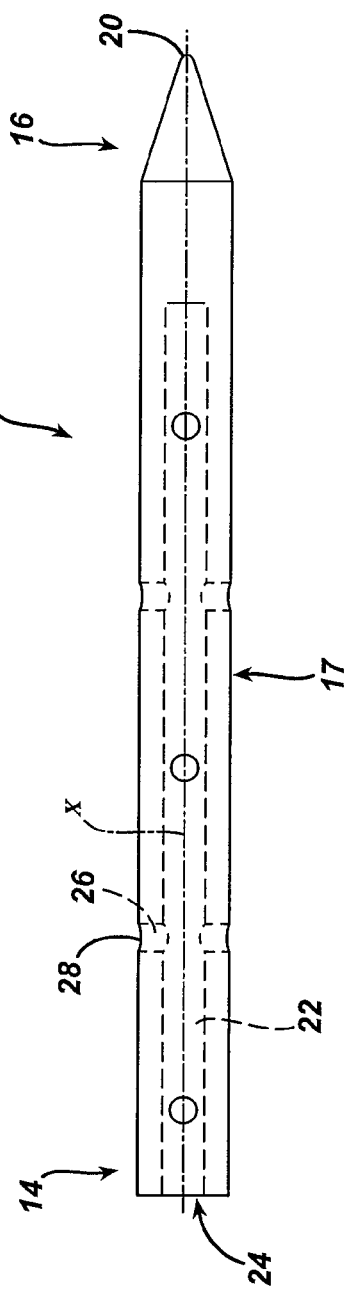
FIG. 2 is a partially transparent side view of the embodiment shown in FIG. 1.
Figure 3:
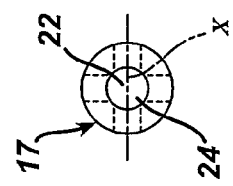
FIG. 3 is a partially transparent view of the proximal end of the embodiment of FIG. 1.

FIGS. 1 through 3 illustrate one embodiment of the fixation device 10, including a body 12 having a proximal end 14, a distal end 16, an outer wall 17, and a longitudinal axis x extending therebetween. The body 12 is preferably a rigid member that may exist in a variety of shapes and sizes. In an exemplary embodiment, however, the device 10 is substantially cylindrical in shape, having a substantially constant diameter over a majority of its length. The distal end 16 of the device may include a conical tip 18 to facilitate inserting the device through predrilled holes or incisions. The tip 18 preferably tapers distally to a point 20.

The device 10 also includes an internal cavity 22, which extends distally from an opening 24 formed in the proximal end 14. In one embodiment, the cavity 22 forms a blind bore that terminates proximal of the distal end 16 and the tip 18. The cavity 22 is preferably in fluid communication with the area external to outer wall 17 through a network of pores (not shown) that can be present when the body 12 is formed of porous material. Alternatively, one or more channels 26 are formed in fluid communication between cavity 22 and one or more openings 28 formed in the outer wall 17 of the body. In either embodiment, any fluid or other material injected into cavity 22 can be secreted through openings 28 or pores in the outer wall 17 to the area external to the outer wall 17. The number of openings 28 and/or pores formed in the outer wall 17 may be in the range of about 1 to 100, and more preferably in the range of about 5 to 25.

In the embodiment in which the body 12 is constructed of a porous material which allows a treatment material to pass between internal cavity 22 and outer wall 17, the average pore diameter is in the range of about 0.01 mm to 5 mm. One skilled in the art will be able to determine the appropriate pore density.

As noted above, the cavity 22 preferably has a length that is less than the length of the body 12, enabling the cavity 22 to terminate proximal to the distal end 16. One skilled in the art will appreciate that the dimensions of the cavity should be such that it is able to accept solids, liquids of varying viscosities, and suspensions without sacrificing the structural properties of the body 12. In an exemplary embodiment, the length of the cavity may be in the range of about 30 mm to 35 mm while the diameter of the cavity is in the range of about 0.5 mm to 5 mm.

The channels 26 and openings 28 should likewise be of dimensions sufficient to accommodate the passage of material from within the cavity 22 to a region external to the device 10. Accordingly, the diameter of the channels 26 and openings 28 is in the range of about 0.5 mm to 1.5 mm. It is understood that while the length of the channels 26 will be a function of the diameter of the body 12, this length is generally in the range of about 0.5 to 1.5 mm. One skilled in the art will readily appreciate that the cavity 22 and channels 26 can have a variety of cross sectional shapes, including irregular, circular, oval, rectangular, triangular, etc. One skilled in the art will further appreciate that the cavity 22 and channels 26 can be formed in the body 12 by a variety of techniques, including machining and/or molding.

The body 12 preferably has dimensions that render it suitable for insertion into a patient (such as a patient's joint) and for affixing a tissue graft. The length of the body 12 should be sufficient to span, and remain within, a bone tunnel created in a femur or tibia, for example. The length of the body is preferably in the range of about 15 mm to 65 mm. The diameter of the body 12 also depends on the desired use, but in any event it should be suitable to enable an interference fit within a bone tunnel. In an exemplary embodiment the diameter of the body 12 is in the range of about 1 mm to 10 mm.

Figure 4:
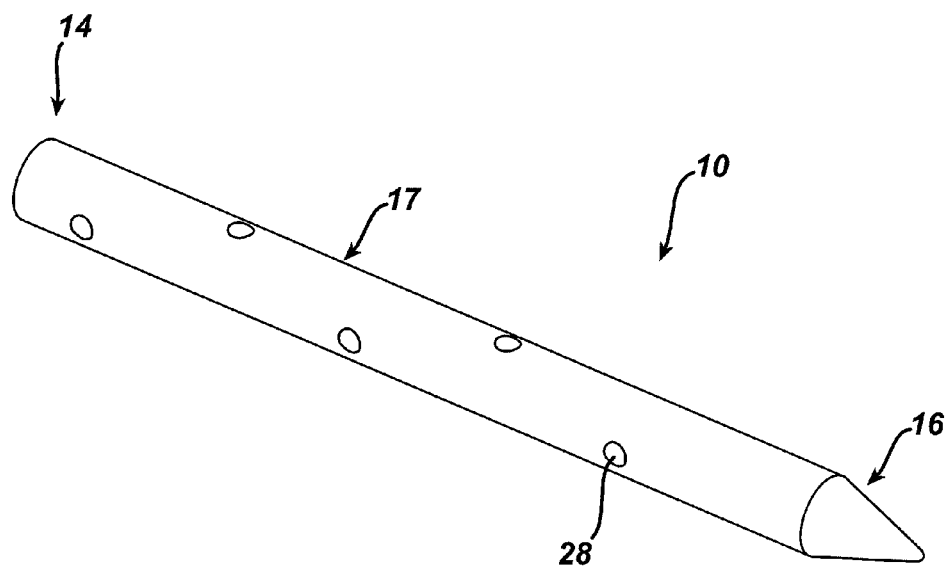
FIG. 4 is a perspective view of the tissue fixation device shown in FIG. 1.

As noted above, the outer wall or surface 17 of the body 12 may be generally smooth and free of surface features, as shown in FIG. 4. Alternatively, the outer wall 17 may include surface features to help hold the device in place after it has been implanted. Such features may include roughened areas, threads, barbs, hooks, and combinations thereof. In one embodiment, the surface features may extend over the entire outer wall 17 or only part of the outer wall 17.

The device 10 is preferably made of a biocompatible, bioresorbable material so that after the body 12 is implanted into a patient to affix tissue, it gradually degrades over time. A person skilled in the art will be able to determine a suitable resorption profile, depending on the desired use of the device, and can tailor the resorption profile by varying the materials used to construct the device 10. Preferably, the device 10 is constructed of materials such that it will fully resorb over a time period in the range of about 12 to 60 weeks.

In one embodiment of the present invention, the device can be formed from a biocompatible polymer including synthetic polymers, natural polymers or combinations thereof. As used herein the term "synthetic polymer" refers to polymers that are not found in nature, even if the polymers are made from naturally occurring biomaterials. The term "natural polymer" refers to polymers that are naturally occurring. In embodiments where the device includes at least one synthetic polymer, suitable biocompatible synthetic polymers can include polymers selected from the group consisting of aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, polyurethanes, poly(ether urethanes), poly (ester urethane), and blends thereof. Suitable synthetic polymers for use in the present invention can also include biosynthetic polymers based on sequences found in collagen, elastin, thrombin, fibronectin, starches, poly(amino acid), poly(propylene fumarate), gelatin, alginate, pectin, fibrin, oxidized cellulose, chitin, chitosan, tropoelastin, hyaluronic acid, ribonucleic acids, deoxyribonucleic acids, polypeptides, proteins, polysaccharides, polynucleotides and combinations thereof.

For the purpose of this invention aliphatic polyesters include, but are not limited to, homopolymers and copolymers of lactide (which includes lactic acid, D-,L- and meso lactide); glycolide (including glycolic acid); ε-caprolactone; p-dioxanone (1,4-dioxan-2-one); trimethylene carbonate (1,3-dioxan-2-one); alkyl derivatives of trimethylene carbonate; δ-valerolactone; β-butyrolactone; γ-butyrolactone; ε-decalactone; hydroxybutyrate; hydroxyvalerate; 1,4-dioxepan-2-one (including its dimer 1,5,8,12-tetraoxacyclotetradecane-7,14-dione); 1,5-dioxepan-2-one; 6,6-dimethyl-1,4-dioxan-2-one; 2,5-diketomorpholine; pivalolactone; α,α diethylpropiolactone; ethylene carbonate; ethylene oxalate; 3-methyl-1,4-dioxane-2,5-dione; 3,3-diethyl-1,4-dioxan-2,5-dione; 6,6-dimethyl-dioxepan-2-one; 6,8-dioxabicycloctane-7-one and polymer blends thereof. Aliphatic polyesters used in the present invention can be homopolymers or copolymers (random, block, segmented, tapered blocks, graft, triblock, etc.) having a linear, branched or star structure. Poly(iminocarbonates), for the purpose of this invention, are understood to include those polymers as described by Kemnitzer and Kohn, in the *Handbook of Biodegradable Polymers*, edited by Domb, et. al., Hardwood Academic Press, pp. 251-272 (1997). Copoly(ether-esters), for the purpose of this invention, are understood to include those copolyester-ethers as described in the Journal of Biomaterials Research, Vol. 22, pages 993-1009, 1988 by Cohn and Younes, and in Polymer Preprints (ACS Division of Polymer Chemistry), Vol. 30(1), page 498, 1989 by Cohn (e.g., PEO/PLA). Polyalkylene oxalates, for the purpose of this invention, include those described in U.S. Pat. Nos. 4,208,511; 4,141,087; 4,130,639; 4,140,678; 4,105,034; and 4,205,399. Polyphosphazenes, co-, ter- and higher order mixed monomer based polymers made from L-lactide, D,L-lactide, lactic acid, glycolide, glycolic acid, para-dioxanone, trimethylene carbonate and E-caprolactone such as are described by Allcock in *The Encyclopedia of Polymer Science*, Vol. 13, pages 31-41, Wiley Intersciences, John Wiley & Sons, 1988 and by Vandorpe, et al in the *Handbook of Biodegradable Polymers*, edited by Domb, et al., Hardwood Academic Press, pp. 161-182 (1997), both of which are incorporated by reference herein. Polyanhydrides include those derived from diacids of the form HOOC—$C_6H_4$—O—$(CH_2)_m$—O—$C_6H_4$—COOH, where "m" is an integer in the range of from 2 to 8, and copolymers thereof with aliphatic alpha-omega diacids of up to 12 carbons. Polyoxaesters, polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213; 5,700,583; and 5,859,150. Polyorthoesters such as those described by Heller in *Handbook of Biodegradable Polymers*, edited by Domb, et al., Hardwood Academic Press, pp. 99-118 (1997).

As used herein, the term "glycolide" is understood to include polyglycolic acid. Further, the term "lactide" is understood to include L-lactide, D-lactide, blends thereof, and lactic acid polymers and copolymers.

As noted above, the device of the present invention is preferably formed from a bioresorbable or bioabsorbable material that has the ability to resorb in a timely fashion in the body environment. The differences in the absorption time under in vivo conditions can also be the basis for combining two different copolymers when forming the device of the present invention. For example, a copolymer of 35:65 ε-caprolactone and glycolide (a relatively fast absorbing polymer) can be blended with 40:60 ε-caprolactone and L-lactide copolymer (a relatively slow absorbing polymer) to form a biocompatible tissue fixation device. Depending upon the processing technique used, the two constituents can be either randomly inter-connected bicontinuous phases, or the constituents could have a gradient-like architecture in the form of a laminate type composite with a well integrated interface between the two constituent layers. The microstructure of the body 12 can be optimized for the desired use and for secure tissue fixation.

In an exemplary embodiment, the device 10 is made from polylactic acid, with or without an additive such as tricalcium phosphate.

In another embodiment, it is desirable to use polymer blends to form a device which transitions from one composition to another composition in a gradient-like architecture. For example, by blending an elastomer of ε-caprolactone-co-glycolide with ε-caprolactone-co-lactide (e.g., with a mole ratio of about 5:95) a device device may be formed that transitions from a softer spongy material to a stiffer more rigid material, for example, in a manner similar to the transition from cartilage to bone. Clearly, one skilled in the art will appreciate that other polymer blends may be used for similar gradient effects, or to provide different gradients (e.g., different absorption profiles, stress response profiles, or different degrees of elasticity). For example, such design features can establish porous areas which allow the transportation of treatment material through predetermined paths.

In embodiments where the device includes at least one natural polymer, suitable examples of natural polymers include, but are not limited to, fibrin-based materials, collagen-based materials, hyaluronic acid-based materials, glycoprotein-based materials, cellulose-based materials, silks and combinations thereof.

In another embodiment of the present invention, the device can be formed from a biocompatible ceramic material. Suitable biocompatible ceramic materials include, for example, hydroxyapatite, α-tricalcium phosphate, β-tricalcium phosphate, bioactive glass, calcium phosphate, calcium sulfate, calcium carbonate, xenogeneic and allogeneic bone material and combinations thereof. Suitable bioactive glass materials for use in the present invention include silicates containing calcium phosphate glass, or calcium phosphate glass with varying amounts of solid particles added to control resorption time. Suitable compounds that may be incorporated into the calcium phosphate bioactive glass include, but are not limited to, magnesium oxide, sodium oxide, potassium oxide, and combinations thereof.

In use, the device 10 of the present invention is advantageous for fixation of bone, tissue, or tissue grafts, and, in an exemplary embodiment, for procedures which require femoral and/or tibial fixation of ACL replacements. The procedure for replacing an ACL includes harvesting a graft, such as autogeneic tissue harvested from elsewhere in the body, and using the graft, secured with the device of the present invention, to replace the damaged ACL. A person skilled in the art will appreciate that in addition to autogeneic tissue, a variety of biocompatible materials, including allogeneic material and synthetic materials, may be used to construct a graft to be affixed with the device of the present invention.

The harvested graft can include both bone-tendon-bone grafts and soft tissue grafts. The bone-tissue-bone grafts are harvested as a single unit including a section of bone or a "bone plug" connected to one side of an elongate tendon region and, preferably, a second bone plug connected to the other side. Alternatively, the graft may be a soft tissue graft formed primarily from tendon such as semi-t and gracilis tendons, which are harvested and prepared by whip stitching the end, or ends, to create secure bundles.

Figure 5A:
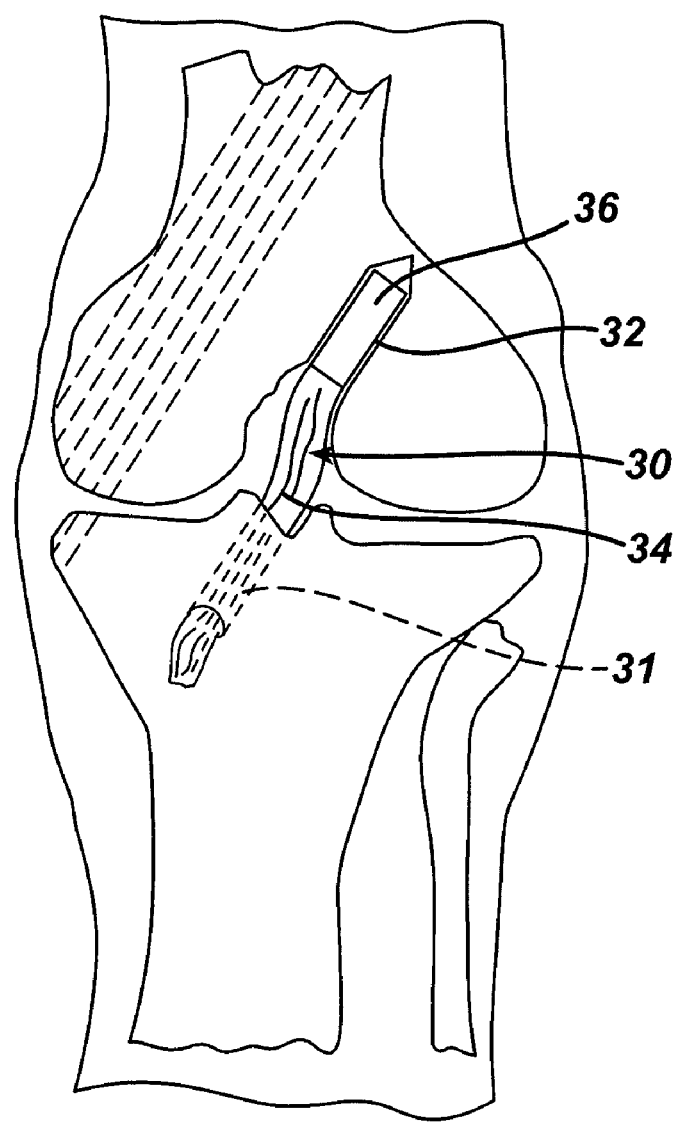
FIGS. 5(A)-5(D) sequentially illustrate a procedure for affixing a tissue graft in the human knee using a fixation device according to the present invention.

In an exemplary technique that utilizes the fixation device of the present invention, bone tunnels are formed in the tibia and the femur at the site where it is desired to position the replacement ACL. The graft is then surgically implanted with the ends of the graft (the bone plug or secure bundle) located in the femoral and tibial bone tunnels. The ends of the graft may then be secured within the tunnels with the fixation device 10 of the present invention. FIG. 5(A) illustrates a graft 30 positioned within a human knee joint such that the ends of the grafts are located in a tibial bone tunnel 31 and a femoral bone tunnel 32. The graft 30 includes a bone plug 36 in the femoral bone tunnel 32 and a tendon section 34 which extends to tibial bone tunnel 31.

Figure 5B:
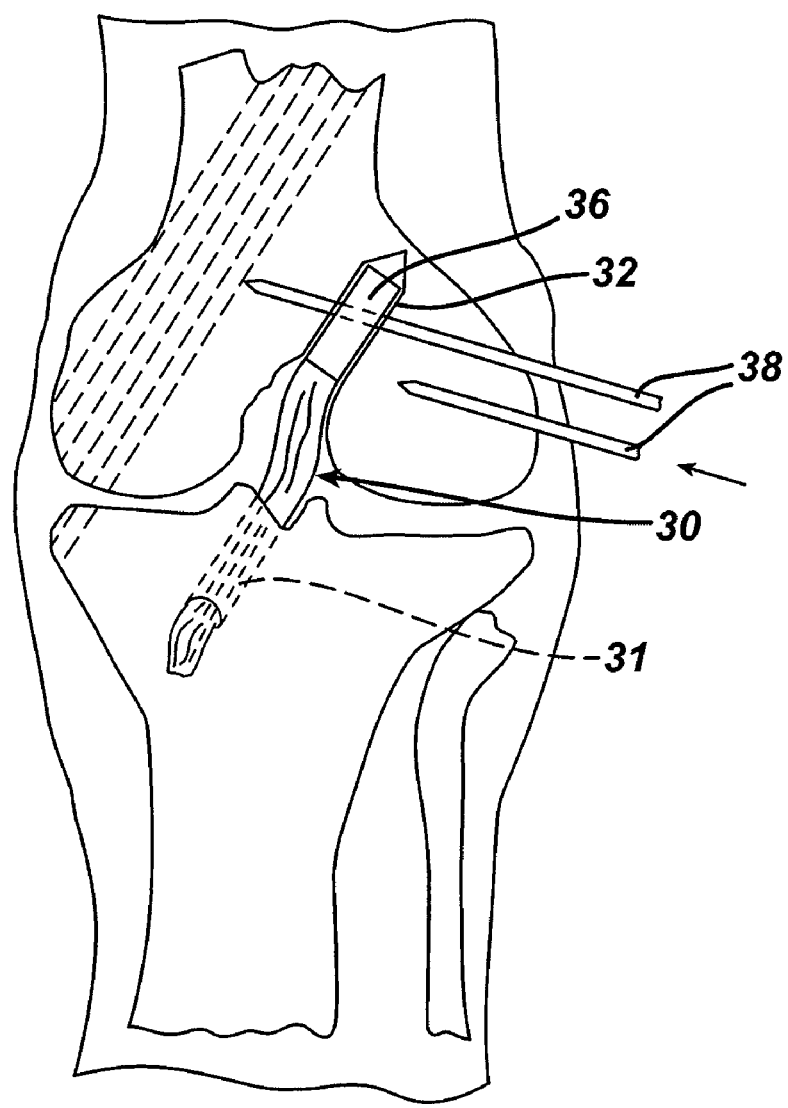
Figure 5C:
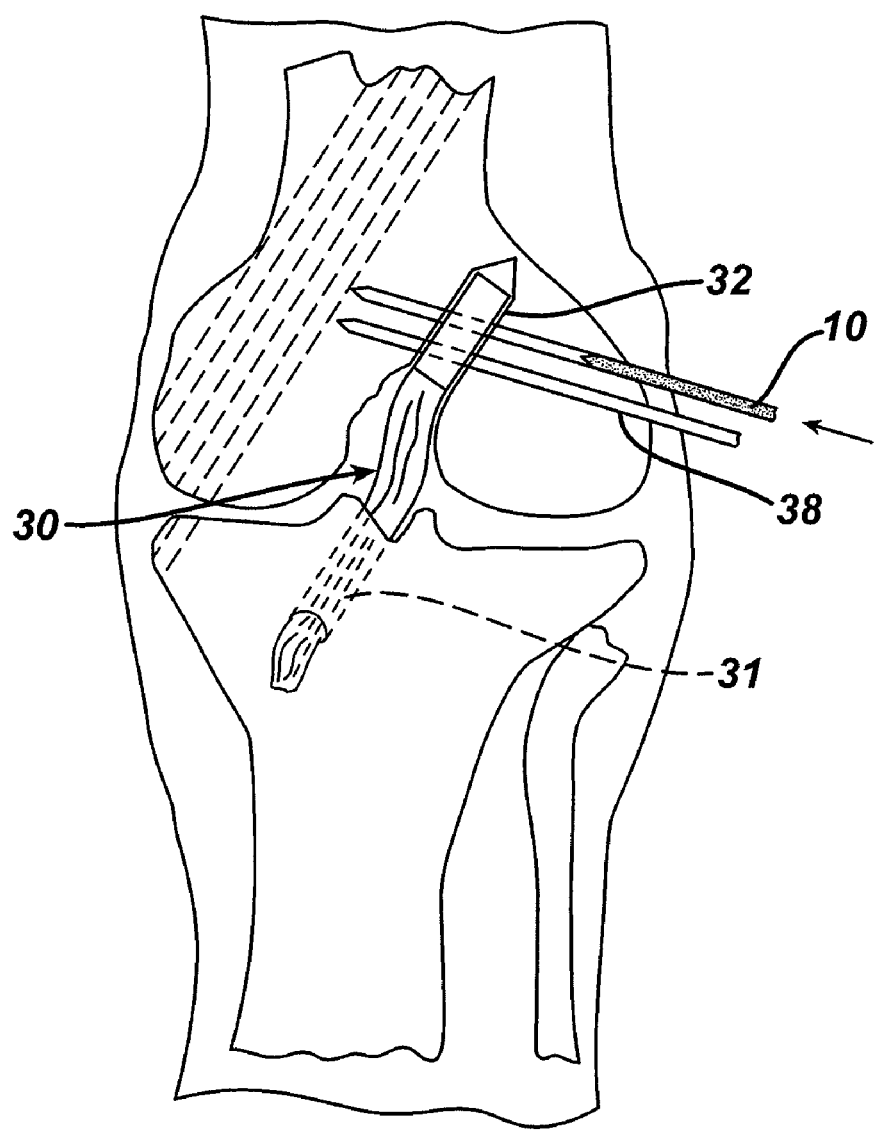

With the graft positioned within the femoral bone tunnel 32, one or more passages 38 can be formed which intersect the femoral bone tunnel 32, and which can accommodate the fixation device 10, as shown in FIG. 5(B). The passages 38 may be formed such that they pass through the graft positioned in the bone tunnel, particularly in the case of a bone-tendon-bone graft. Once passages 38 are formed, the device 10 can be inserted through the passages 38 to secure the graft 30 as illustrated in FIG. 5(C).

The fixation device 10 secures the graft 30 by extending through the graft and across the bone tunnel 32. In the case of either a bone-tendon-bone graft or a soft tissue graft, the device 10 can pass directly through the graft thereby suspending the graft within the bone tunnel. In addition, insertion of the device 10 can compress the graft against the bone tunnel sidewall to create bone-to-graft contact and to promote healing.

Figure 5D:
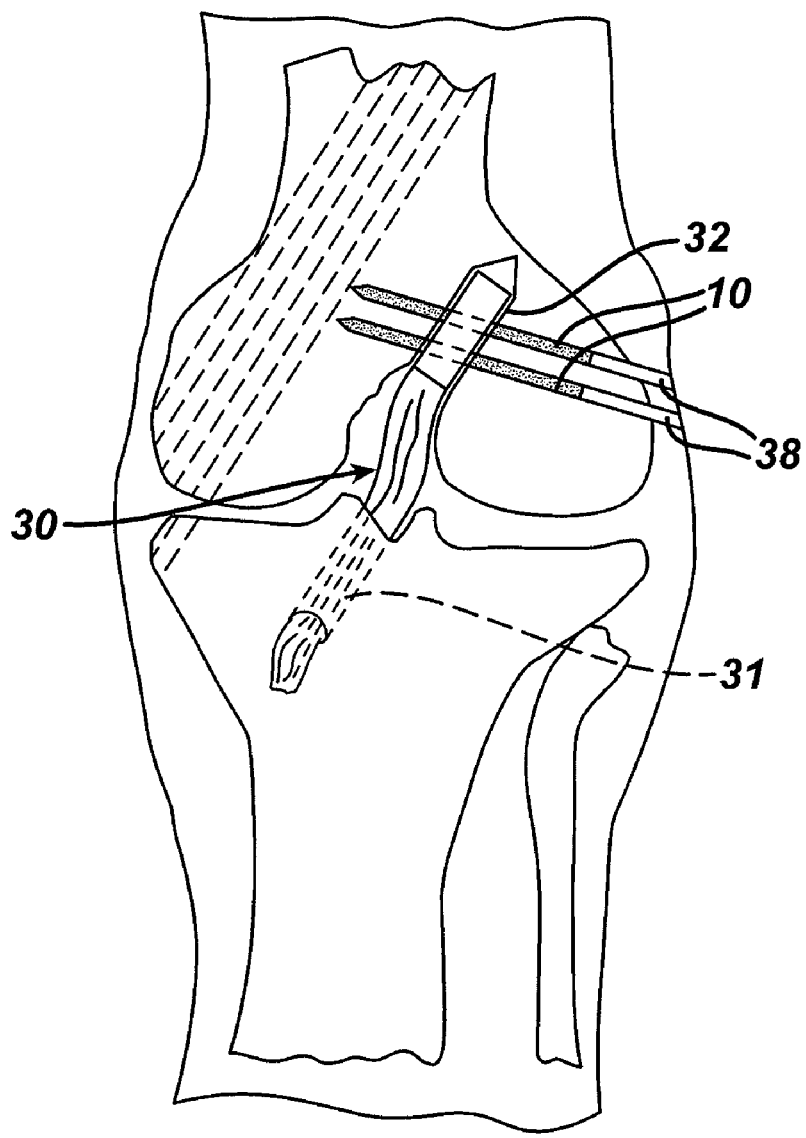

FIG. 5(D) illustrates the graft 30 fixed within the femoral bone tunnel by two fixation devices 10 positioned within two passages 38. The tibial end of the graft remains within the tibial bone tunnel 31 and can be fixed in position using a similar procedure, or it can be fixed with other methods known to one skilled in the art.

Once one or more of the fixation devices 10 are implanted as described above, a treatment material can be delivered to the surgical site through the internal cavity 22. In one embodiment, the treatment material is delivered to the internal cavity 22 of the device 10 prior to surgical placement of the device, and the treatment material is then secreted through the outer wall 17 after placement. In an alternative embodiment, treatment material is delivered into the internal cavity 22 after implanting the fixation device within the patient. The treatment material, which may be a solid, a liquid or a suspension, can be injected into the internal cavity 22 through an opening at the proximal end 24 of the body 12, and out of the device through either the channels 26 in the outer wall 17 or through a porous outer wall.

The treatment material can be delivered uniformly over the outer surface 17 of the device, or alternatively its delivery can be concentrated in certain areas of the outer surface 17. For example, excess treatment material may be delivered to the graft-bone contact area so as to promote adhesion and to speed healing. One skilled in the art will realize that control of the distribution of the treatment material to the exterior of the body 12 may be achieved through various means, such as by adjusting the placement of the openings, the size of the openings, porosity, the delivery pressure, the viscosity of the treatment material, and combinations thereof.

In one embodiment, the treatment material is a biologically active material and/or an adhesive, which may also be biological in origin. Such materials include, but are not limited to, hyaluronic acid, fibrin glue, fibrin clot, collagen gel, alginate gel, gelatin-resorcin-formalin adhesive, mussel-based adhesive, dihydroxyphenylalanine (DOPA) based adhesive, chitosan, transglutaminase, poly(amino acid)-based adhesive, cellulose-based adhesive, polysaccharide-based adhesive, synthetic acrylate-based adhesives, platelet rich plasma (PRP), platelet poor plasma (PPP), clot of PRP, clot of PPP, Matrigel, Monostearoyl Glycerol co-Succinate (MGSA), Monostearoyl Glycerol co-Succinate/polyethylene glycol (MGSA/PEG) copolymers, laminin, elastin, proteoglycans, and combinations thereof.

The adhesive material may also include a suitable cross-linking agent, for example, divinyl sulfone (DVS), polyethylene glycol divinyl sulfone (VS-PEG-VS), hydroxyethyl methacrylate divinyl sulfone (HEMA-DIS-HEMA), formaldehyde, glutaraldehyde, aldehydes, isocyanates, alkyl and aryl halides, imidoesters, N-substituted maleimides, acylating compounds, carbodiimide, hydroxychloride, N-hydroxysuccinimide, light (e.g., blue light and UV light), pH, temperature, and combinations thereof.

In another embodiment, the treatment material may be a biologically active component that, when present at the site of injury, promotes healing and/or regeneration of the affected tissue. In addition to being compounds or agents that actually promote or expedite healing, the biologically active component may also include compounds or agents that prevent infection (e.g., antimicrobial agents and antibiotics), compounds or agents that reduce inflammation (e.g., anti-inflammatory agents), compounds that prevent or minimize adhesion formation, such as oxidized regenerated cellulose (e.g., INTERCEED and Surgicel®, available from Ethicon, Inc.), hyaluronic acid, and compounds or agents that suppress the immune system (e.g., immunosuppressants).

By way of example, other types of biologically active components which can be delivered with the device of the present invention can include tissue fragments, heterologous or autologous growth factors, proteins (including matrix proteins), peptides, antibodies, enzymes, platelets, glycoproteins, hormones, cytokines, glycosaminoglycans, nucleic acids, analgesics, viruses, virus particles, and cell types. It is understood that one or more biologically active component of the same or different functionality may be delivered.

Examples of suitable biologically active components include the multitude of heterologous or autologous growth factors known to promote healing and/or regeneration of injured or damaged tissue. Exemplary growth factors include, but are not limited to, TGF-β, bone morphogenic protein, cartilage-derived morphogenic protein, fibroblast growth factor, platelet-derived growth factor, vascular endothelial cell-derived growth factor (VEGF), epidermal growth factor, insulin-like growth factor, hepatocyte growth factor, and fragments thereof. Suitable biologically active components likewise include the agonists and antagonists of the agents noted above. The growth factor can also include combinations of the growth factors listed above. In addition, the growth factor can be an autologous growth factor that is supplied by platelets in the blood. In this case, the growth factor from platelets will be an undefined cocktail of various growth factors.

The proteins that may be delivered through the internal cavity of the device of the present invention include proteins that are secreted from a cell or other biological source, such as, for example platelets, that are present within the cavity. The isolated form of a protein typically is one that is about 55% or greater in purity, i.e., isolated from other cellular proteins, molecules, debris, etc. More preferably, the isolated protein is one that is at least 65% pure, and most preferably one that is at least about 75 to 95% pure. Notwithstanding the above, one skilled in the art will appreciate that proteins having a purity below about 55% are still considered to be within the scope of this invention. As used herein, the term "protein" embraces glycoproteins, lipoproteins, proteoglycans, peptides, and fragments thereof. Examples of proteins useful as biologically active components include, but are not limited to, pleiotrophin, endothelin, tenascin, fibronectin, fibrinogen, vitronectin, V-CAM, I-CAM, N-CAM, selectin, cadherin, integrin, laminin, actin, myosin, collagen, microfilament, intermediate filament, antibody, elastin, fibrillin, and fragments thereof.

Glycosaminoglycans, highly charged polysaccharides which play a role in cellular adhesion, may also serve as biologically active components according to the present invention. Exemplary glycosaminoglycans useful as biologically active components include, but are not limited to, heparan sulfate, heparin, chondroitin sulfate, dermatan sulfate, keratan sulfate, hyaluronan (also known as hyaluronic acid), and combinations thereof.

The device can also deliver cells, including, but not limited to, osteocytes, osteoblasts, osteoclasts, fibroblasts, stem cells, pluripotent cells, chondrocyte progenitors, chondrocytes, endothelial cells, macrophages, leukocytes, adipocytes, monocytes, plasma cells, mast cells, umbilical cord cells, stromal cells, mesenchymal stem cells, epithelial cells, myoblasts, tenocytes, ligament fibroblasts, neurons, and bone marrow cells. Cells typically have at their surface receptor molecules which are responsive to a cognate ligand (e.g., a stimulator). A stimulator is a ligand which when in contact with its cognate receptor induce the cell possessing the receptor to produce a specific biological action. For example, in response to a stimulator (or ligand) a cell may produce significant levels of secondary messengers, like $Ca^{+2}$, which then will have subsequent effects upon cellular processes such as the phosphorylation of proteins, such as (keeping with our example) protein kinase C. In some instances, once a cell is stimulated with the proper stimulator, the cell secretes a cellular messenger usually in the form of a protein (including glycoproteins, proteoglycans, and lipoproteins). This cellular messenger can be an antibody (e.g., secreted from plasma cells), a hormone, (e.g., a paracrine, autocrine, or exocrine hormone), a cytokine, or natural or synthetic fragments thereof.

The device of the invention can also be used with gene therapy techniques in which nucleic acids, viruses, or virus particles deliver a gene of interest, which encodes at least one gene product of interest, to specific cells or cell types. Accordingly, the biological biologically active component can be a nucleic acid (e.g., DNA, RNA, or an oligonucleotide), a virus, a virus particle, or a non-viral vector. The viruses and virus particles may be, or may be derived from, DNA or RNA viruses. The gene product of interest is preferably selected from the group consisting of proteins, polypeptides, interference ribonucleic acids (iRNA) and combinations thereof.

Once the applicable nucleic acids and/or viral agents (i.e., viruses or viral particles) are incorporated into the internal cavity of the device, the nucleic acid or viral agent can be taken up by cells, and any proteins that they encode can be produced locally by the cells. In one embodiment, the nucleic acid or viral agent can be taken up by the cells within the internal cavity or, in an alternative embodiment, the nucleic acid or viral agent can be taken up by the cells in the tissue surrounding the site outer wall 17. One skilled in the art will recognize that the protein produced can be a protein of the type noted above, or a similar protein that facilitates an enhanced capacity of the tissue to heal an injury or a disease, combat an infection, or reduce an inflammatory response. Nucleic acids can also be used to block the expression of unwanted gene product that may impact negatively on a tissue repair process or other normal biological processes. DNA, RNA and viral agents are often used to accomplish such an expression blocking function, which is also known as gene expression knock out.

One skilled in the art will appreciate that the identity of the biologically active component may be determined by a surgeon, based on principles of medical science and the applicable treatment objectives. One skilled in the art will also appreciate further features and advantages of the invention based on the above-described embodiments. Accordingly, the invention is not to be limited by what has been particularly shown and described, except as indicated by the appended claims.

What is claimed is:

1. A bioimplantable tissue fixation device, comprising:
   an elongate body formed of a biocompatible, bioresorbable material and having an outer surface, a proximal end, a distal end and a longitudinal axis extending therethrough;
   an internal cavity extending into the body from an opening in the proximal end of the body, the internal cavity terminating proximal to the distal end; and
   at least one opening formed in the outer surface of the body, each of the at least one openings being in fluid communication with the internal cavity such that the internal cavity is able to accept a treatment material for delivery external to the outer surface of the body through the at least one opening.

2. The fixation device of claim 1, wherein the elongate body is a pin adapted to secure bone and/or soft tissue graft.

3. The fixation device of claim 2, wherein the elongate body is constructed of polymers or copolymers formed from monomers selected from the group consisting of lactide; glycolide; ε-caprolactone; hydroxybuterate; hydroxyvalerate; 1,4-dioxepan-2-one; 1,5,8,12-tetraoxyacyclotetradecane-7,14-dione; 1,5-dioxepan-2-one; 6,6-dimethyl-1,4-dioxan-2-one; 2,5-diketomorpholine; p-dioxanone (1,4-dioxan-2-one); trimethylene carbonate (1,3-dioxan-2-one); alkyl derivatives of trimethylene carbonate; δ-valerolactone; β-butyrolactone; γ-butyrolactone, ε-decalactone; pivalolactone; α,α-diethylpropiolactone; ethylene carbonate; ethylene oxalate; 3-methyl-1,4-dioxane-2,5-dione; 3,3-diethyl-1,4-dioxan-2,5-dione; and 6,8-dioxabicycloctane-7-one.

4. The fixation device of claim 1, wherein the elongate body is formed of a polymer or copolymer selected from the group consisting of polylactic acid, aliphatic polyesters, poly(amino acids), poly(propylene fumarate), copoly(etheresters), polyalkylene oxalates, polyamides, tyrosine-derived polycarbonates, poly(iminocarbonates), polyorthoesters, polyoxaesters, polyamidoesters, polyoxaesters containing amine groups, poly(anhydrides), polyphosphazenes, polyurethanes, poly(ether urethanes), poly(ester urethane), biosynthetic polymers and combinations thereof.

5. The fixation device of claim 2, wherein the elongate body has a length in the range of about 15 mm to 65 mm.

6. The fixation device of claim 1, wherein at least a portion of the outer surface of the elongate body includes surface features for holding the elongate body in position after it has been implanted.

7. The fixation device of claim 6, wherein the surface features are selected from the group consisting of roughened regions, threads, barbs, hooks, and combinations thereof.

8. The fixation device of claim 1, wherein the outer surface of the elongate body is smooth.

9. The fixation device of claim 1, wherein the outer surface of the elongate body is porous and the at least one opening formed in the outer surface results from a pore matrix extending between the internal cavity and the outer surface.

10. The fixation device of claim 1, wherein the at least one opening communicates with the internal cavity through at least one passageway.

11. The fixation device of claim 10, wherein the outer surface is non-porous.

12. The fixation device of claim 2, wherein the diameter of the pin is in the range of about 1 mm to 10 mm.

13. The fixation device of claim 2, wherein the resorption profile of the pin is in the range of about 12 to 60 weeks.

14. The fixation device of claim 1, wherein the diameter of the internal cavity is in the range of about 0.5 mm to 5 mm.

15. The fixation device of claim 9, wherein the pores have an average pore diameter in the range of about 0.01 mm to 5 mm.

16. The fixation device of claim 1, wherein the treatment material is a biologically active material.

17. The fixation device of claim 16, wherein the biologically active material is selected from the group consisting of tissue fragments, growth factors, proteins, analgesics, antibodies, enzymes, cytokines, glycosaminoglycans, viruses, virus particles, nucleic acids, peptides, isolated cells, platelets, and combinations thereof.

18. The fixation device of claim 1, wherein the treatment material is an adhesive agent.

19. The fixation device of claim 18, wherein the adhesive agent comprises an anchoring agent selected from the group consisting of hyaluronic acid, fibrin glue, fibrin clot, collagen gel, gelatin-resorcin-formalin adhesive, mussel-based adhesive, dihydroxyphenylalanine (DOPA) based adhesive, chitosan, transglutaminase, poly(amino acid)-based adhesive, cellulose-based adhesive, synthetic acrylate-based adhesives, platelet rich plasma (PRP), Matrigel, Monostearoyl Glycerol co-Succinate (MGSA), Monostearoyl Glycerol co-Succinate/polyethylene glycol (MGSA/PEG) copolymers, laminin, elastin, proteoglycans and combinations thereof.

20. The fixation device of claim 18, wherein the adhesive agent comprises a chemical cross-linking agent selected from the group consisting of divinyl sulfone (DVS), polyethylene glycon divinyl sulfone (VS-PEG-VS), hydroxyethyl methacrylate divinyl sulfone (HEMA-DIS-HEMA), formaldehyde, glutaraldehyde, aldehydes, isocyanates, alkyl and aryl halides, imidoesters, N-substituted maleimides, acylating compounds, carbodiimide, hydroxychloride, N-hydroxysuccinimide, light, pH, temperature, and combinations thereof.

21. The fixation device of claim 10, wherein the at least one opening formed in the outer surface of the body includes a number of openings in the range of about 5 to 25.

22. The fixation device of claim 10, wherein the diameter of the at least one opening is in the range of about 0.5 mm to 1.5 mm.

23. The fixation device of claim 1, wherein the elongate body has a substantially cylindrical shape.

24. The fixation device of claim 1, wherein the distal end of the elongate body tapers to a point.

25. A method for attaching a tissue graft to bone, comprising:
 forming a bone tunnel into bone;
 providing a tissue fixation device in the form of an elongate member having a longitudinally oriented channel formed therein that extends from an opening in a proximal end thereof, the tissue fixation device having at least one opening formed in a sidewall thereof that is in fluid communication with the channel;
 positioning a portion of the tissue graft within the bone tunnel;
 inserting the tissue fixation deice within the bone tunnel to secure the tissue graft therein; and
 injecting a treatment material into the channel of the tissue fixation device to enable the material to be secreted through the at least one opening to a region external to the sidewall of the tissue fixation device.

26. The method of claim 25, wherein the treatment material is a biologically active material.

27. The method of claim 26, wherein the biologically active material is selected from the group consisting of tissue fragments, growth factors, proteins, analgesics, antibodies, enzymes, cytokines, glycosaminoglycans, viruses, virus particles, nucleic acids, peptides, isolated cells, platelets, and combinations thereof.

28. The method of claim 25, wherein the treatment material is an adhesive agent.

29. The method of claim 28, wherein the adhesive agent comprises an anchoring agent selected from the group consisting of hyaluronic acid, fibrin glue, fibrin clot, collagen gel, gelatin-resorcin-formalin adhesive, mussel-based adhesive, dihydroxyphenylalanine (DOPA) based adhesive, chitosan, transglutaminase, poly(amino acid)-based adhesive, cellulose-based adhesive, polysaccaride-based adhesive, synthetic acrylate-based adhesive, polyurethane-based adhesive, platelet rich plasma (PRP), platelet poor plasma (PPP), Matrigel, Monostearoyl Glycerol co-Succinate (MGSA), Monostearoyl Glycerol co-Succinate/polyethylene glycol (MGSA/PEG) copolymers, laminin, elastin, proteoglycans, and combinations thereof.

30. The method of claim 28, wherein the adhesive agent comprises a cross-linking agent selected from the group consisting of divinyl sulfone (DVS), polyethylene glycon divinyl sulfone (VS-PEG-VS), hydroxyethyl methacrylate divinyl sulfone (HEMA-DIS-HEMA), formaldehyde, glutaraldehyde, aldehydes, isocyanates, alkyl and aryl halides, imidoesters, N-substituted maleimides, acylating compounds, carbodiimide, hydroxychloride, N-hydroxysuccinimide, light, pH, temperature, and combinations thereof.

* * * * *